United States Patent [19]
Tazuma et al.

[11] 4,087,477
[45] May 2, 1978

[54] METHOD OF REDUCING THE α-ACETYLENE CONTENT OF HYDROCARBON

[75] Inventors: James J. Tazuma, Stow; Angelo Bergomi, Akron, both of Ohio

[73] Assignee: The Goodyear Tire & Rubber Company, Akron, Ohio

[21] Appl. No.: 745,890

[22] Filed: Nov. 29, 1976

[51] Int. Cl.$^2$ .............................................. C07C 7/00
[52] U.S. Cl. ........................................... 260/681.5 R
[58] Field of Search ..................................... 260/681.5

[56] References Cited

U.S. PATENT DOCUMENTS

| | | | |
|---|---|---|---|
| 2,373,715 | 4/1945 | Soday | 260/681.5 R |
| 2,398,973 | 4/1946 | Soday | 260/681.5 R |
| 3,951,754 | 4/1976 | Liakumorich et al. | 260/681.5 R |
| 3,992,471 | 11/1976 | Priegnitz | 260/681.5 R |

*Primary Examiner*—Veronica O'Keefe
*Attorney, Agent, or Firm*—J. D. Wolfe

[57] ABSTRACT

Hydrocarbon fraction containing diolefins and α-acetylenes are treated with base-modified catalyst to reduce the α-acetylene content. The base-modified catalyst comprises a support such as alumina containing an alkali metal hydroxide and related bases.

8 Claims, No Drawings

METHOD OF REDUCING THE α-ACETYLENE CONTENT OF HYDROCARBON

This invention relates to a method of removing α-acetylenes from diolefins containing from 4 to 8 carbon atoms and mixtures of said diolefins with monoolefins and hydrocarbons.

The presence of α-acetylenes such as 1-pentyne and 1-penten-4-yne in isoprene and mixtures of isoprene with monoolefins and hydrocarbons (hereinafter called polymerization stocks) has been known to act as a poison for the catalyst, viz. transition catalyst, used to make polymers and stereospecific rubbers of polyisoprene, for example, the high cis- or trans-type polymers, as well as other diolefin rubbers. Consequently, these polymerization stocks have been treated to remove or neutralize the α-acetylenes present prior to the polymerization step, or larger amounts of catalyst had to be used due to its being poisoned by the impurities.

We have discovered that α-acetylenes contained in a polymerization stock can be isomerized in the presence of a base-modified catalyst. The isomerized acetylenes so obtained can be easily removed from the polymerization stock, since they have a boiling point considerably higher than their precursors. More particularly, the separation of 1-pentyne (boiling point (b.p.) 40° C.) and 1-penten-4-yne (b.p. 43° C.) from isoprene (b.p. 34° C.) is complicated by the fact that these compounds have close boiling points. The removal of the last traces of these acetylenes is especially difficult. However, 1-pentyne and 1-penten-4-yne contained in an isoprene stream can be isomerized to 2-pentyne (b.p. 56° C.) and 1-penten-3-yne (b.p. 59° C.) by contacting the said stream with a base-modified catalyst. The isomerized acetylenes can then be effectively removed from the isoprene in view of their higher boiling points.

The base-modified catalyst used for the isomerization of the α-acetylenes consist of inert supports modified by the addition of suitable bases. The supports which can be used include silicates and carbonates of the alkali metals (Group IA of the Periodic System), oxides, silicates and carbonates of the alkaline earth metals (Group IIA of the Periodic System), oxides of metals of Groups IIB, IVB, VIB of the Periodic System, as well as oxides of metals which are known as supports or carriers. The supports are modified by the addition of inorganic bases. These bases can be sodamide, alkali metal acetylides, alkali metal alkoxides, and alkali metal hydroxides. The concentration of the base on the support can range between 5 and 40 percent by weight, the preferred range being between 10 and 30 percent. Alumina loaded with potassium and/or sodium hydroxide is a preferred catalyst in view of its low cost and ease of handling. The alkali hydroxide, after being dispersed or wet on the support, is dried to remove water and preferably activated at temperatures in excess of 500° C. in a stream of inert gas such as argon or nitrogen. It should be emphasized that this activation step is advantageous, but not essential for the isomerization of the α-acetylenes.

We have further discovered that the time of contact of the base-modified catalyst with the polymerization stock can be controlled to regulate the level of α-acetylenes in stock so the α-acetylene level will not interfere with the polymerization catalyst. Thus, by contacting at a liquid hourly space velocity (LHSV) between 0.5 to 20 and preferably 1 to 5, the α-acetylene content of the polymerization stocks can be connected to less volatile products which can be readily separated by fractional distillation. Usually the temperature for the above treatment is controlled between 50 to 200° C. with the preferred range being 50° to 150° C. Pressures above or below atmospheric can be used. Also, the process can be practiced by running continuously or batchwise without the need for solvents or other reactants at high velocities and under mild temperature and pressure conditions, viz. either with fixed bed or fluidized bed operation.

The polymerization stocks of primary usefulness in this invention are the so-called $C_4$, $C_5$, $C_6$, $C_7$, and $C_8$ streams or distillation cuts available as a byproduct of crude oil refining or cracking operations. The so-called $C_4$, $C_5$, etc. cuts or streams generally designate a distillation fraction composed of hydrocarbons containing the number of carbon atoms designated by the subscript. Side streams relatively rich in olefins or diolefins are available as products of the refining and cracking operations and the amount of diolefins can be increased by suitable cracking of the appropriate cut of the desired boiling range and/or fractionation of the streams. Then these cracked or distillate cuts rich in diolefins such as isoprene, butadiene, 1,3-pentadiene, sometimes called the $C_4$ and $C_5$ cuts can be used for polymerization stocks after removal of the impurities or catalyst poisons.

The nature of this invention and its advantages can be more readily seen from the following illustrative examples, wherein all parts and percentages are by weight unless otherwise indicated.

EXAMPLE I

Preparation of the Catalyst

The support, for example, alumina, was impregnated with a dilute aqueous solution containing the desired amount of alkali hydroxide, 5 to 10 percent by weight of water. The bulk of the water was removed at 50° to 60° C. under reduced pressure. The dry support was charged into the reactor where it was activated at 550° C. for 2 hours in a stream of argon.

Some examples to illustrate the range of application of the catalyst are reported below. In these examples, Alcoa H151 TM alumina was used as the support.

EXAMPLE II

The reactor consisted of a stainless steel tube 30 cm. long and 9.5 mm. ID, packed with a layer of stainless steel packing, a layer of catalyst (5 cc.) and another layer of packing. The reactor was heated with an electric furnace. The feed was metered through the catalyst bed at the desired flow rate. The starting material and the isomerized products were analyzed by gas chromatography.

An isoprene stream was passed over 10 percent KOH/alumina at 100° C. and LHSV = 6. The composition of the starting material and of the isomerized product are reported below. As it can be seen, a substantial conversion of the α-acetylenes to their internal isomers was achieved:

|  | Starting Material | Isomerized Product |
|---|---|---|
| n-Pentane | 1.8 | 2.0 |
| C$_5$ Olefins | 6.6 | 7.2 |
| Isoprene | 89.2 | 88.2 |
| 1-Pentyne | 1.1 | 0.4 |
| 2-Pentyne | — | 0.8 |

-continued

|  | Starting Material | Isomerized Product |
|---|---|---|
| 1-Penten-4-yne | 1.2 | — |
| 1-Penten-3-yne | — | 1.1 |
| Others | 0.1 | 0.3 |

EXAMPLE III

The isoprene stream described in Example II was contacted with 20 percent KOH/alumina at 100° C. and LHSV equal 2 to give an isomerized product with the following composition:

| n-Pentane | 1.8 |
|---|---|
| $C_5$ Olefins | 6.7 |
| Isoprene | 89.2 |
| 1-Pentyne | tr |
| 2-Pentyne | 1.1 |
| 1-Penten-4-yne | — |
| 1-Penten-3-yne | 1.0 |
| Others | 0.2 |

A complete conversion of the α-acetylenes to their internal isomers was achieved.

EXAMPLE IV

An isoprene stream was passed over 30 percent KOH/alumina at 100° C. and LHSV equal 2. The composition of the starting material and of the isomerized product are reported below:

|  | Starting Material | Isomerized Product |
|---|---|---|
| n-Pentane | 1.8 | 1.7 |
| $C_5$ Olefins | 6.4 | 6.1 |
| Isoprene | 87.0 | 88.0 |
| 1-Pentyne | 2.2 | 0.1 |
| 2-Pentyne | — | 1.9 |
| 1-Penten-4-yne | 2.5 | — |
| 1-Penten-3-yne | — | 2.0 |
| Others | 0.1 | 0.2 |

EXAMPLE V

An isoprene stream was contacted with 20 percent KOH/alumina at 100° C. and LHSV equal 2. The composition of the starting material and of the isomerized product are reported below:

|  | Starting Material | Isomerized Product |
|---|---|---|
| n-Pentane | 21.7 | 21.7 |
| 1-Pentene | 1.1 | 1.1 |
| 2-Methyl-1-Butene | 3.3 | 3.3 |
| t-2-Pentene | 0.2 | 0.2 |
| Isoprene | 73.7 | 73.7 |

-continued

|  | Starting Material | Isomerized Product |
|---|---|---|
| 1-Pentyne | 120 ppm* | — |
| 2-Pentyne | — | 105 |
| 1-Penten-4-yne | 160 ppm | — |
| 1-Penten-3-yne | — | 105 |
| Heavies | — | tr |

*ppm = parts per million.

EXAMPLE VI

The isoprene stream used in Example IV was contacted 20 percent NaOH/alumina at 100° C. and LHSV equal 2 to give an isomerized product similar to that reported in the previous example.

The hydrocarbon fractions from Examples II to VI were subjected to distillation in a fractionation column to take overhead the isoprene and to leave in the bottom of the fractionation tower those hydrocarbons boiling higher than isoprene. Generally, the isoprene fraction obtained had an end point on distillation of less than 50° C.

The isoprene cut obtained from fractionation could be polymerized with the transition metal high cis catalyst to high cis polyisoprene. Similar results may be obtainable when sodium hydroxide or the other alkali metal hydroxides were substituted in Example I to prepare the catalyst for use in Examples II to VI.

While certain representative embodiments and details have been shown for the purpose of illustrating the invention, it will be apparent to those skilled in this art that various changes and modifications may be made therein without departing from the spirit or scope of the invention.

What is claimed is:

1. A method of reducing the α-acetylene content of a hydrocarbon fraction which comprises a diolefin containing 4 to 8 carbon atoms and α-acetylenic impurities by contacting said hydrocarbon fraction with a base modified catalyst comprising an inert support treated with an alkali metal hydroxide, connecting the α-acetylenes to their higher boiling isomers and separating said isomers from the isoprene by fractional distillation.

2. The method of claim 1 wherein the base-modified catalyst consists of alkali hydroxides supported on alumina.

3. The method of claim 1 wherein the contacting is at a LHSV of 0.5 to 20.

4. The method of claim 1 wherein the hydrocarbon fraction contacts the alkali hydroxide at 50° to 150° C.

5. The method of claim 1 wherein the alkali is sodium.

6. The method of claim 1 wherein the alkali is potassium.

7. The method of claim 5 wherein the fraction contains butadiene.

8. The method of claim 7 wherein the fraction contains isoprene.

* * * * *